US005505931A

United States Patent [19]
Pribish

[11] Patent Number: 5,505,931
[45] Date of Patent: Apr. 9, 1996

[54] ACID CLEAVABLE COMPOUNDS, THEIR PREPARATION AND USE AS BIFUNCTIONAL ACID-LABILE CROSSLINKING AGENTS

[75] Inventor: James R. Pribish, Midland, Mich.

[73] Assignee: The Dow Chemical Company, Midland, Mich.

[21] Appl. No.: 26,800

[22] Filed: Mar. 4, 1993

[51] Int. Cl.$^6$ .............. A61K 43/00; C07D 307/60; C07D 307/94; C07D 307/89
[52] U.S. Cl. .............. 424/1.11; 549/233; 549/237; 549/247
[58] Field of Search .............. 424/1.11; 549/233, 549/237, 240, 247

[56] References Cited

U.S. PATENT DOCUMENTS

| | | | |
|---|---|---|---|
| 4,542,225 | 9/1985 | Blattler et al. | 548/473 |
| 4,569,789 | 2/1986 | Blattler et al. | 260/112 R |
| 4,618,492 | 10/1986 | Blattler et al. | 424/85 |
| 4,631,190 | 12/1986 | Shen et al. | 424/85 |
| 4,647,671 | 3/1987 | Schwartz | 548/545 |
| 4,764,368 | 8/1988 | Blattler et al. | 424/85 |
| 4,885,363 | 12/1989 | Tweedle et al. | 540/465 |
| 5,045,312 | 9/1991 | Aston et al. | 424/85.8 |
| 5,053,503 | 10/1991 | Dean et al. | 540/474 |
| 5,057,302 | 10/1991 | Johnson et al. | 424/1.1 |
| 5,094,848 | 3/1992 | Brixner | 424/85.91 |
| 5,094,849 | 3/1992 | Cullinan et al. | 424/85.91 |

FOREIGN PATENT DOCUMENTS

| | | |
|---|---|---|
| 0253202A2 | 1/1988 | European Pat. Off. . |
| 0318948A2 | 6/1989 | European Pat. Off. . |
| 0328147A2 | 8/1989 | European Pat. Off. . |
| 8600527 | 1/1986 | WIPO . |
| 89/12631A1 | 12/1989 | WIPO ............ C07D 257/02 |
| 9003188 | 4/1990 | WIPO . |
| 9003401 | 4/1990 | WIPO . |
| 9014844 | 12/1990 | WIPO . |
| 9112023 | 8/1991 | WIPO . |

OTHER PUBLICATIONS

Shen et al., "CIS-Aconityl Spacer Between Daunomycin and Macromolecular Carriers: A Model of pH-Sensitive Linkage Releasing Drug from a Lysosomotropic Conjugate", *Biochemical and Biophysical Research Communications*, V. 102, No. 3, 1048–1054, Oct. 15, 1981.

Dillman et al., "Comparisons of Drug and Toxin Immunoconjugates", *Antibody, Immunoconjugates and Radiopharmaceuticals*, V. 1, No. 1, 65–77 (1988).

Meares et al., "Chelate Radiochemistry: cleavable Linkers Lead to Altered Levels of Radioactivity in the Liver", *Int. J. Cancer*, Supplement 2, 99–102 (1988).

Srinivasachar et al., "New Protein Cross-Linking Reagents That are Cleaved by Mild Acid", *Biochemistry*, V. 28, 2501–2509 (1989).

Ding et al., "Application of Target–specific Drug Immunoconjugates to Experimental Bone Marrow Replacement Therapy in Mice", *Cancer Research*, V. 50, 1538–1543, Mar. 1, 1990.

Hudecz et al., "Immunoconjugate Design: A Predictive Approach for Coupling of Daunomycin to Monoclonal Antibodies", *Bioconjugate Chem.*, V. 1, 197–204 (1990).

Koch et al., "The Oxidative Cleavability of Protein Cross–Linking Reagents Containing Organoselenium Bridges", *Bioconjugate Chem.*, vol. 1, 296–304, (1990).

Mueller et al., "Antibody Conjugates with Morpholinodoxorubicin and Acid–Cleavable Linkers", *Bioconjugate Chem.*, V. 1, 325–330 (1990).

Kaneko et al., "New Hydrazone Derivatives of Adriamycin and Their Immunoconjugates–a Correlation Between Acid Stability and Cytotoxicity", *Bioconjugate Chemistry*, V. 2, No. 3, May/Jun. 1991.

Greenfield et al., "Evaluation in Vitro of Adriamycin Immunoconjugates Synthesized Using an Acid–sensitive Hydrazone Linker", *Cancer Research*, 50, 6600–6607, Oct. 15, 1990.

Braslawsky et al., "antitumor Activity of Adriamycin (Hydrazone–linked) Immunoconjugates Compared with Free Adriamycin and Specificity of Tumor Cell Killing", *Cancer Research*, V. 50, 6608–6614, Oct. 15, 1990.

Amsberry et al., "The Lactonization of 2'–Hydroxyhydrocinnamic Acid Amides: A Potential Prodrug for Amines", *J. Org. Chem.*, V. 55, 5867–5877 (1990).

Senter et al., "Development of a Drug–Release Strategy Based on the Reductive Fragmentation of Benzyl Carbamate Disulfides", *J. Org. Chem.*, V. 55, 2975–2978 (1990).

Ahmad et al., "Daunorubicin Coupled to Monoclonal Antibodies Via a cis–Aconitic Anhydride Linker: Biochemical and Cytotoxic Properties Revisited", *Anticancer Research*, V. 10, 837–844 (1990).

Neville et al., "Enhancement of Immunotoxin Eficacy by Acid–Cleavable Cross–linking Agents Utilizing Diphtheria Toxin and Toxin Mutants", *J. of Biological Chemistry*, V. 264, No. 25, 14653–14661 (1989).

Dillman et al., "superiority of an Acid–labile Daunorubicin–Monoclonal Antibody Immunoconjugate Compared to Free Drug", *Cancer Research*, V. 48, 6097–6102, Nov. 1, 1988.

Buchardt et al., "Protein Crosslinking Reagents Containing a Selenoethylene Linker are Cleaved by Mild Oxidation", *Analytical Biochemistry*, 158, 87–92 (1986).

*Primary Examiner*—Philip Tucker

[57] ABSTRACT

Novel compounds, their preparation and their use as bifunctional acid-labile crosslinking agents which are cleavable in an acid environment at a pH of below about 5.0 allowing for the controlled release of nucleophilic groups attached thereto are disclosed.

4 Claims, No Drawings

ACID CLEAVABLE COMPOUNDS, THEIR PREPARATION AND USE AS BIFUNCTIONAL ACID-LABILE CROSSLINKING AGENTS

BACKGROUND OF THE INVENTION

This invention relates to delivering diagnostic or biologically active compounds to targeted cells and controlled release of these compounds.

A reoccurring problem in medicine is that due to the lack of specificity of the agents used for treatment of a disease, the patient is often the recipient of a new set of maladies from the therapy. This scenario is especially common in the treatment of various forms of cancer where a therapeutic agent will exert its toxic affect on nontargeted normal tissues, in addition to cancerous cells.

To circumvent the nonspecificity of a therapeutic agent, the agent can be coupled to a carrier that possesses some degree of specificity for a particular cell. For example, carrier molecules such as liposomes, proteins and antibodies have been used in conjunction with a broad spectrum of diagnostic and therapeutic agents.

The development of monoclonal antibodies (MAbs), which have a specific recognition and affinity for certain selected antigens, has led to the delivery of diagnostic therapeutic agents to selected cells via immunoconjugates. "Immunoconjugates" are covalently bonded hybrid molecules composed of a target directing moiety (recognition portion), such as an antibody molecule, and an effector molecule, such as a toxin, drug, biological response modifier, or a radioisotope.

Although the MAb carrier system enhances delivery of the therapeutic agent to specific targeted cells, other problems remain. One problematic area includes situations where the agent is only active, or at least more potent, when free from the MAb carrier. Another problematic area is that although MAb are designed to be specific for a particular antigen, some sorption or binding to nontargeted cells will occur resulting in destruction of normal cells. The latter problem occurs, for example, when the immunoconjugate contain a radionuclide. The radioactivity has a tendency to localize nonspecifically in the kidney, potentially exerting undesirable renal toxicity and thereby lowering the therapeutic index of the immunoconjugate. To overcome these noted problems, linkers, which act as a bridge to join the therapeutic agent and and target directing moiety, have been developed which have a cleavable bond to release the therapeutic agent. In the latter situation, where there is nonspecific binding to cells, the agent can be cleaved from the carrier and the agent rapidly cleared from the body.

A number of different cleavable linker groups have been previously described. The mechanism for release of an agent from these linker groups include cleavage by reduction of a disulfide bond, by irradiation of a photolabile bond, by hydrolysis of derivatized amino acid side chain, by serum complement-mediated hydrolysis and acid-catalyzed hydrolysis. [See for example, U.S. Pat. No. 5,053,503, PCT Publication WO 86/00527, PCT Publication WO 90/03188, PCT Publication WO 90/03401, PCT Publication WO 90/14844, European Patent Application 0 253 220, and European Patent Application 0 318 948. Some of these mechanisms are susceptible to release of the agent prior to having reached the specific cell, tissue or organ.

U.S. Pat. No. 4,631,190 and Shen et al. *Biochem. Biophys. Res. Commun.*, 102:1048–1054 (1981) disclose a drug attached to the linker through an acidic bonding group, such as carboxyl, that is in a cis configuration with another acidic group, and a targeting moiety which is attached in a cis configuration with another acidic group. In particular, the antitumor antibiotic daunomycin was linked to poly(D-lysine) using cis-aconitic anhydride and a carbodimide coupling agent. In conjugated form, the nitrogen group of daunomycin exists as an amide, the amide compound is biologically inert. When the conjugate is carried into the cell, the acidic lysosomal environment facilitates hydrolysis of the amide bond to generate free daunomycin.

When using essentially the same method to attach a monoclonal antibody specific for cancer cells to daunomycin with cis-aconitic anhydride, the immunoconjugate was found to be selectively carried into tumor cells where hydrolysis took place to generate free daunomycin. The presence of free daunomycin led to tumor regression in animal tests. [See, for example, Benton et al., in *Anthracycline Antibiotics*, H. S. El Khadem, Ed., Academic Press, New York pp. 1–57 (1982); Oki, *Stud. Biophys.*, 104:169–200 (1984); Kumar et al., *Can. J. Chem.*, 62:2585–2591 (1984): and Cassinelli, *J. Antibiot.*, 38:856–867 (1984)]. (Control experiments with antibody alone, drug alone, or a mixture of antibody and free drug (unconjugated) resulted in an inferior response.)

Blattler et al., in U.S. Pat. No. 4,569,789, describe a drug delivery system which is formed by reaction of an active substance with a maleic anhydride moiety. The active substance is released upon cleavage of the amide bond. The patent discloses that at pH 5, 15 percent is cleaved after five hours and after five hours at pH 4, less than 50 percent is cleaved.

Blattler et al., in U.S. Pat. No. 4,764,368 disclose heterobifunctional reagents, developed from cyclohexenemaleamic acid, that are cleavable under mildly acidic condition. The heterobifunctional reagents were used for linking the drug gelonin to antibodies, which provides for intracellular release of the drug at the targeted cells. No data was presented for cleavage of the drug from the conjugate.

Thus there remains a need for a carrier agent conjugate which releases the agent by cleavage under mild conditions. Furthermore, it would be advantageous to provide a complex that does not readily dissociate outside the targeted cell, exhibits rapid whole body clearance except from the desired tissue, and conjugates readily with an effector molecule.

SUMMARY OF THE INVENTION

The present invention is directed to compounds corresponding to one of the the Formulae

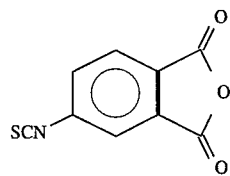

I

-continued

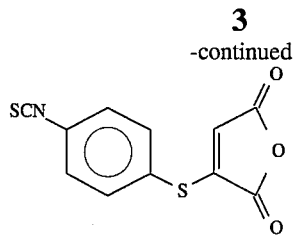

II or

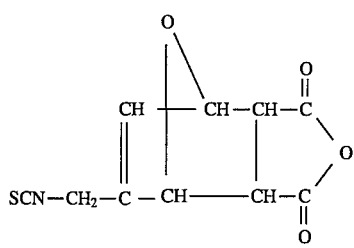

III

The present invention is also directed to the preparation of novel compounds and their use as heterobifunctional acid-labile crosslinking or linker agents which are cleavable in an acid environment, for example, at a pH of below about 5.0, allowing for the controlled release of a nucleophilic effector moiety attached thereto.

The present invention further relates to a class of conjugate materials containing a diagnostic or biologically active therapeutic agent as an effector molecule and a site specific directing molecule, which conjugate materials release the effector molecule in the acidic environment such as occurs within a lysosome of a cell in which the materials are ingested. In a preferred embodiment, the conjugate materials are an acid cleavable conjugate comprising an effector moiety containing an amino group, a target directing moiety and an acid cleavable linker, wherein the conjugate is represented by one of the following Formulae:

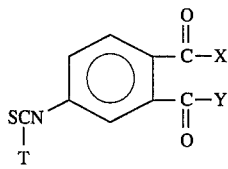

IV

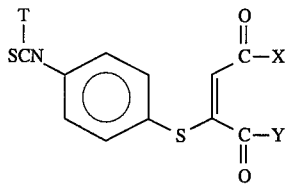

V or

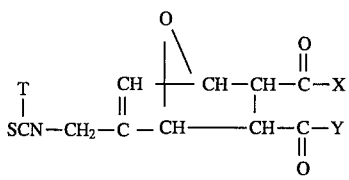

VI wherein one of X and Y is O— and the other of X and Y is an effector moiety containing an amino group whose amino nitrogen forms an amide link with a carbonyl group of the anhydride and T is a target directing moiety.

Additionally, the present invention relates to an approach for delivering a therapeutic or biologically active agent to a selected cell site and to the controlled release of the therapeutic or biologically active agent from the carrier conjugates whereby undesirable diseased or malignant cells can be destroyed or diagnosed without harming normal cells. In this procedure, the product of this invention is directed, delivered and bound to the diseased or malignant cells by a group which is a target directing moiety.

An advantage of the conjugates of the present invention is their stability at a neutral pH as is present in the serum and their rapid cleavage under acid conditions, e.g., pH below about 5.5. Specifically, intracellular organelles such as lysosomes exhibit an acidic microenvironment of about 4.5 to 5.5. Thus, when the target directing moiety of the conjugate is a monoclonal antibody, or fragment thereof, specific to a cell surface antigen and the effector moiety is a chelate comprising a radionuclide bound by a chelating agent, the conjugate will remain substantially intact at the outside of the cell.

If the conjugate is bound non-specifically to non-targeted cells, the conjugate will be ingested by the cells. The amide linkage cleaved by the acidic pH of the lysosome. The cleavage of the amide bond between the linker and chelate produces a free chelate which can then be rapidly cleared from the body.

DETAILED DESCRIPTION OF THE INVENTION

The present invention provides for the preparation of novel compounds for use as bifunctional acid-labile linking agents. The present invention also provides a method for delivery of an effector moiety to a particular target tissue comprising administering to a human or mammalian host a conjugate comprising an effector moiety attached to a target directing moiety through a linker that is selectively cleaved at one or more target sites. The conjugate can be represented by the formula

E—L—P          V wherein E represents an effector moiety; P represents a target directing moiety; and L represents an acid clearable linker.

The linkers of the present invention are represented by Formulae I, II and III

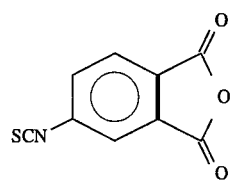

I

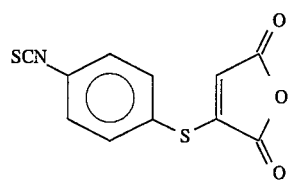

II or

III

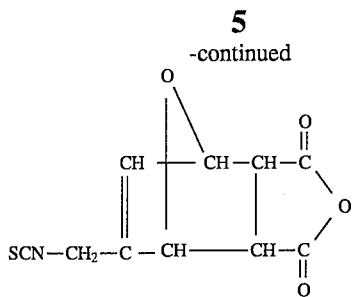

The linkers of Formulae I–III can by synthesized as illustrated by the following general reaction schemes 1, 2 and 3 using commercially available starting material.

-continued
Scheme 1

(a) Tetrahydrofuran, room temperature for 10 minutes, then relflux for 1 hour.
(b) Reflux for 2 hours Scheme 2

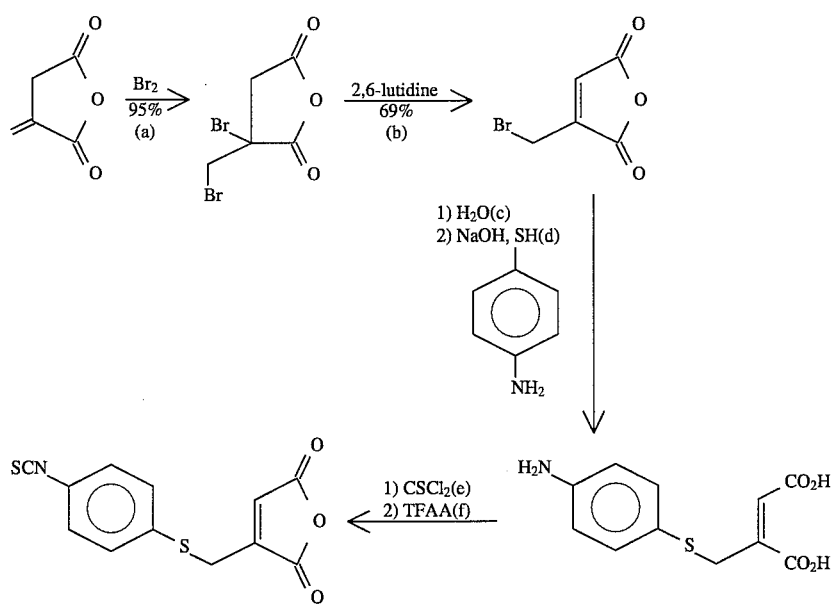

(a) CH$_2$Cl$_2$, room temperature for 15 minutes. Then reflux for 1.5 hours
(b) Toluene, 0° for 25 mL, then room temperature for 60 minutes
(c) H$_2$O at room temperature for 1 hour
(d) 3.0 eq. NaOH, H$_2$O room temperature for 21 hours.
(e) CHCl$_3$ H$_2$O reflux for 2 hours
(f) CHCl$_3$, reflux, 1 hour Scheme 1

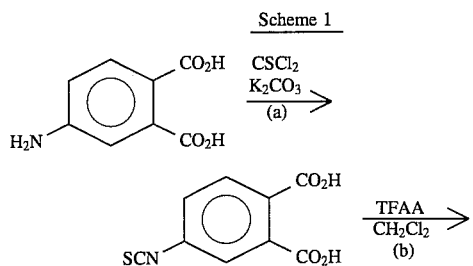

Scheme 3

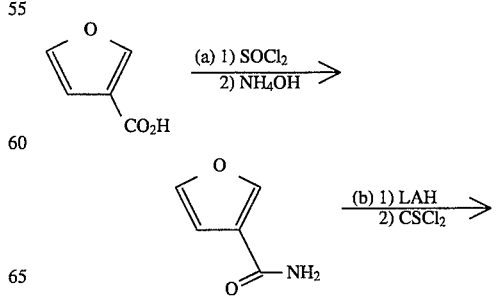

-continued
Scheme 3

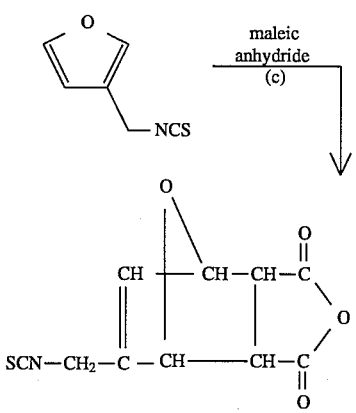

(a) 1) Reflux at room temperature for 1 hour
    2) 0–5° C. for 10 minutes then room temperature for 1.5 hours (b) 1) THF, reflux for 2 hours
    2) CHCl$_3$, NaHCO$_3$, H$_2$O, 0–5° C. for 45 minutes (c) Ether, 16 hours at room temperature The linkers of the present invention connect an effector moiety to a targeting moiety, the targeting moiety is usually a peptide or protein.

An effector moiety for use in the present invention is a diagnostic or therapeutic agent and generally contains an available nucleophilic group which will react with the anhydride group of the linker to form a covalent bond. Preferably the effector moiety contains a free primary or secondary amine or be capable of being modified to contain a free amine group which will react with the anhydride group of the linker to form an amide linkage. The effector moiety is preferably released from the linker under acidic conditions, i.e., below pH 5.5, without alteration of its structure and activity.

Any suitable diagnostic agent may be used with the linkers of the present invention. It is generally necessary for the diagnostic agent to be bound to the linker by means of a chelating agent or other molecule which contains a nucleophilic group. Examples of diagnostic agents are diagnostic radionuclides, such as, $^{67}$Cu, $^{67}$Ga, $^{99m}$Tc, $^{123}$I, $^{125}$I, $^{131}$I, $^{153}$Sm, $^{166}$Ho, and $^{177}$Lu; nuclear magnetic resonance contrast agents, such as Gd$^{+3}$, Mn$^{+2}$, Mn$^{+3}$ and Fe$^{+3}$; X-ray contrast agents, and other imaging agents. These agents are detected by external means.

In another embodiment of the invention, the effector moiety is a therapeutic agent. Suitable therapeutic agents include therapeutically effective radioisotopes and therapeutic drugs. Therapeutic radioisotopes include, for example, $^{166}$Ho, $^{153}$Sm, $^{177}$Lu, $^{115m}$In, $^{165}$Dy, $^{90}$Y, $^{146}$La. $^{159}$Gd, $^{111}$In, $^{175}$Yb, and $^{47}$Sc. Preferably the radioisotope is $^{166}$Ho, $^{153}$Sm, $^{177}$Lu or $^{115m}$In. Examples of cytotoxic or antineoplastic drugs are methotrexate; pyrimidine analogs, such as fluorouracil and deoxyuridine; cytosine arabinoside, purine analogs, such as thioguanine, mercaptopurine and azathiopurine; vinca alkaloids, such as vincristine and vinblastine; actinomycin D; daunorubicin, doxorubicin, and other anthracycline derivatives; belomycin; mitomycin; ricin A-chain; abrin A-chain; modecin A-chain as well as gelonin and other single-chain ribosomal inactivating proteins. Other therapeutic agents useful in the present invention are polypeptide growth factors. Examples of such factors are platelet-derived growth factors, insulin-like growth factors, transforming growth factor, fibroblast growth factors including acidic fibroblast growth factor and basic fibroblast growth factor, epidermal growth factory nerve growth factor and bone morphogenetic proteins. The therapeutic agent may also be a toxin, such as pokeweed antiviral proteins PAP, PAPII and PAP-S.

The type of therapeutic agent chosen for use will vary according to the nature of the patient's illness. The radionuclides may be bound to the linker by a chelating agent in the form of stable complex called a chelate. Preferably, the chelate is a molecule that is rapidly excreted in the urine if administered in its free form.

The targeting molecules used with the linkers of the present invention bind to a desired target site in vivo. The targeting molecules may bind to a receptor, substrate, antigenic determinant, or other binding site on a target cell or tissue. Examples of targeting proteins include antibodies, enzymes (e.g., fibrinolytic enzymes), biologic response modifiers (e.g., interleukins, interferons, erythropeoitin, or colony stimulating factors), peptide hormones, and fragments thereof. Preferably, the targeting moiety contains a free amino group, such as contained in lysine residues, to react with the isothiocyanate group of the linker.

In one embodiment of the invention, the targeting protein is a monoclonal antibody or monoclonal antibody fragment. A number of monoclonal antibodies that bind to a specific type of cell have been developed, including MAbs specific for tumor-associated antigens in humans. Antibodies derived through genetic engineering or protein engineering may be employed as well. The antibody employed in the present invention may be an intact molecule, a fragment thereof, or a functional equivalent thereof. Examples of antibody fragments are F(ab')2. Fab', Fab and Fv fragments, which may be produced by conventional methods, or by genetic or protein engineering. Engineered antibodies referred to as single chain antibodies also may be used. Chimeric antibodies, of which one portion is derived from one species, and another portion is derived from another species may be obtained and used in the present invention. Such antibodies or antibody fragments may be commercially available or may be made by standard somatic cell hybridization techniques.

Examples of a suitable monoclonal antibodies are CC antibodies, a series of monoclonal antibodies specific for TAG-72 (tumor associated glycoprotein) described in published PCT Application No. WO 89/00692, on Jan. 26, 1989, and published PCT application WO 90/04410, on May 3, 1990. The preferred CC antibody is CC49. The antibodies OKT3 and OKT4, which are antibodies that bind to peripheral T-cells and human t-helper cells, respectively, may be used with the linkers of the present invention. OKT3 and OKT4 are produced by hybridomas ATCC CRL 8001 and CRL 8002, respectively. An anti-transferrin receptor antibody, useful for tumor therapy and produced by ATCC culture H884 is another example of aminoclonal antibody which an e used with the liners of the present invention. Generally, the linker and protein are mixed in a molar ratio of greater than 1:10 and less than about 100:1 depending on the protein and protein concentration. Ratios of about 0.5:1 to about 4:1 are preferred.

Conjugation of the target directing moiety to the linkers of the present invention occurs by reaction of the isothiocyanate moiety with a free amine, such as that present on lysine, to form a thiourea covalent bond. This reaction generally involves reacting the linker with the amine containing target directing moiety from 2 to 18 hours in an aqueous buffered solution at pH 6 to 10 at room temperature. Alternatively, the isothiocyanate can be reacted with hydrazine to form a semicarbazide that can react with a sugar aldehyde moiety of the constant region of an antibody.

Targeting proteins serve to deliver the effector moiety to a desired target site in vivo. An example of such a target site is a tumor. However, targeting proteins are rarely completely specific for the target tissue, and a portion of an administered conjugate commonly localized on one or more non-target tissues through such mechanisms as cross-reactive binding and non-specific uptake, including uptake into excretory organs such as liver and kidneys.

In accordance with the present invention, the problems associated with localization of the conjugates at non-target sites can be reduced by separating the effector moiety of the conjugate from the targeting protein by cleaving the linker holding the conjugate together. While not wishing to be bound by theory, it is believed that when the effector moiety is a radioactive chelate and the targeting directing moiety is an antibody, the advantageous results of the present invention are obtained for the following reasons: When the conjugate goes to the target cell and the recognitions site is on the cell surface, the conjugate will not be exposed to an environment sufficiently acidic to cleave a significant amount of the chelate from the linker. The radionuclide will thus remain at the target site and produce a cytotoxic affect. If the conjugate goes to a non-target site, such as the liver of kidneys, the conjugate will be internalized by the cell and exposed to the acidic environment of the lysosome. The acidic environment of the lysosome causes the acid-cleavable linker to degrade and release the small chelate. The chelate, without the attached target directing moiety, can be readily eliminated from the body. This effects a reduction of cytotoxic effects on the non-target organ when the effector moiety is a cytotoxic agent, or a reduction of background when the effector moiety is an imaging agent.

If the effector moiety needs to be cleaved from the linker prior to exerting its therapeutic affect, the target directing moiety should be directed to an internal cell marker, where the conjugate would be internalized within the cell and the therapeutic agent released.

The effector molecules and target directing moiety form a complex with the acid cleavable linkers of the present invention wherein the complex is represented by one of the following formulae:

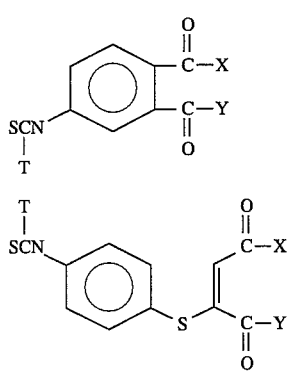

IV

V or

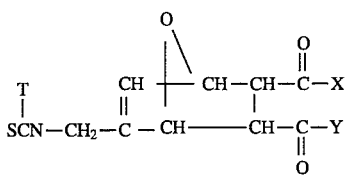

VI wherein one of X or Y is O—; and the other one of X and Y is an effector moiety containing an amino nitrogen and T is a target directing moiety.

When the effector moiety is a radionuclide, imaging agent or contrast agent joined by means of a chelating agent, the chelating agent preferable contains an amine group which is capable of reacting with the anhydride group of the linker. Of particular interest are aminocarboxylic acid chelating agents, aminophosphonic chelating agents and polyaza chelating agents containing secondary and tertiary amines. Preferred polyazamacrocyclic chelating agents are of the formula

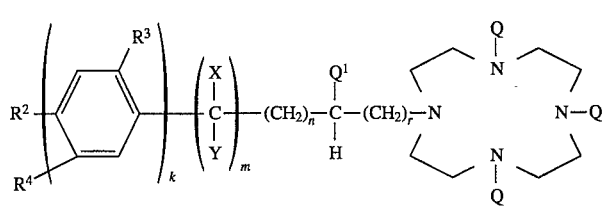

(I)

wherein:
each Q is independently hydrogen, $(CHR^5)_p CO_2 R$, $(CHR^5)_p PO_3 H_2$, or $(CHR^5)_p C(O)NR^5$;
$Q^1$ is $(CHR^5)_w CO_2 R$;
each R independently is hydrogen, benzyl or $C_1$–$C_4$ alkyl; with the proviso that that at least two of the sum of Q and $Q^1$ must be other than hydrogen;
each $R^5$ independently is hydrogen, $C_1$–$C_4$ alkyl or —($C_1$–$C_2$ alkyl)phenyl;
X and Y are each independently hydrogen or may be taken with an adjacent X and Y to form an additional carbon-carbon bond;
k is 1 or 2;
n is 0 or 1;
m is an integer from 0 to 10 inclusive;
p is 1 or 2;
r is 0 or 1;
w is 0 or 1;
with the proviso that n is only 1 when X and/or Y form an additional carbon-carbon bond, and the sum of r and w is 0 or 1;
$R^3$ is $C_1$–$C_4$ alkoxy, —OCH$_2$CO$_2$H, hydroxy or hydrogen;
$R^2$ and $R^4$ are independently hydrogen or amino;
with the proviso that when k is 1, $R^2$ and $R^4$ cannot both be hydrogen but one of $R^2$ and $R^4$ must be hydrogen; and with the further proviso that when k is 0, there is only one $R^2$ or $R^4$ which is an amino.

Preferred amines of the polyaza chelating agents of Formula I are tertiary amines, preferably where r is 0 and each Q is $(CHR^5)_p CO_2 R$.

Procedures for synthesizing polyaza macrocycles are well known in the art.

Examples of preferred chelating agents are given in Table I and are named as follows:

I A is 1-(4-aminophenyl)-1,4,7,10-tetraazacyclododecane-1,4,7,10-tetraacetic acid;

I B is 1-[2-(4-aminophenyl)ethyl]-1,4,7,10-tetraazacyclododecane-1,4,7,10-tetraacetic acid (PA-DOTA);

I C is 1-(5-amino-2-methoxybenzyl)-1,4,7,10-tetraazacyclododecane-4,7,10-triacetic acid;

I D is 1-(5-amino-2-hydroxybenzyl)-1,4,7,10-tetraazacyclododecane-4,7,10-triacetic acid;

I E is 1-[2-(4-aminophenyl)ethyl]-1,4,7,10-tetraazacyclododecane-1-(R,S,-acetic-4,7,10 -tris-(R-methylacetic) acid, the preparation of which is given in European Patent publication no. 0420942, published Apr. 10, 1991, the disclosure of which is hereby incorporated by reference; and I F is 1,4,7,10-tetraaza-1-N-(1-carboxy-3-aminopropyl)-tris-4,7,10-N,N,N-(1-carboxymethyl)cyclododecane (AL-DOTA).

The preparation of IA–ID is given in European Patent publication No. 0353450, published Feb. 7, 1990, and European Patent publication No. 0420942, published Apr. 10, 1991, the disclosures of which are hereby incorporated by reference.

TABLE I

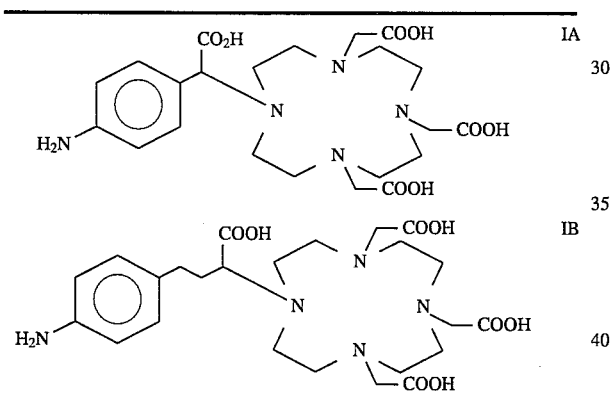

TABLE I-continued

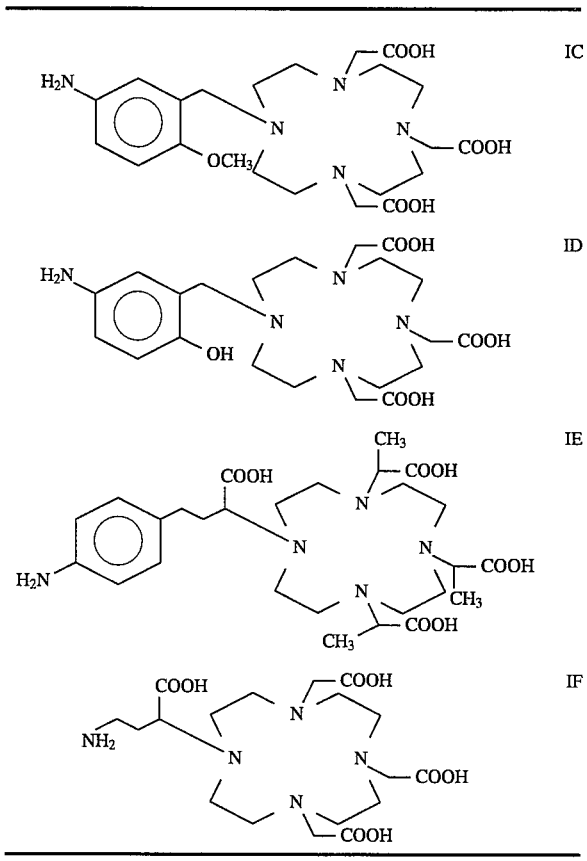

The more preferred chelating agents are PA-DOTA and AL-DOTA.

A general procedure for making chelating agents of the general formula of AL-DOTA is given in Scheme 4.

Scheme 4: Synthesis of Al-DOTA

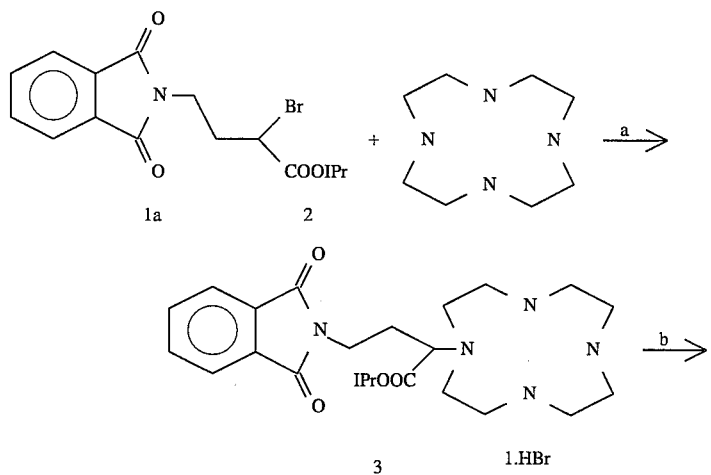

-continued
Scheme 4: Synthesis of A1-DOTA

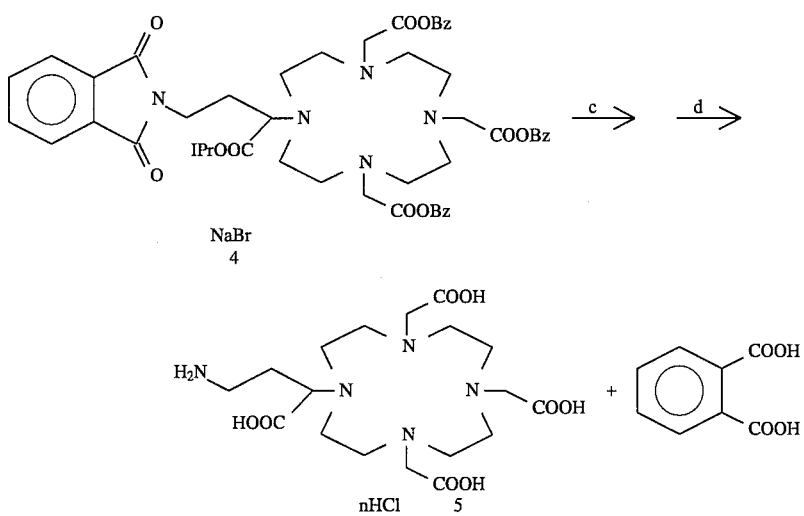

(a) 1.15 eq 2, CHCl3 (78 percent chrom)
(b) 3.05 eq benzyl bromoacetate, K2CO3, dry acetonitrile (28 percent chrom
(c) 10 percent Pd/C, H2 (1 atm), ethanol, H2O
(d) 9N HCl, Δ

Methods for the carboxylation of an amine of a ligand to give amine derivatives containing a carboxyalkyl group are well known, as are the methods which give alkyl phosphonic and hydroxyalkyl substituents on the amine nitrogens. [See, for example, U.S. Pat. Nos. 3,726,912 and 3,398,198, the disclosures of which are hereby incorporated by reference.]

Aminophosphonic acid derivatives of ligands can be prepared by a number of known synthetic techniques. Of particular importance is the reaction of a compound containing at least one reactive amine hydrogen with a carbonyl compound (aldehyde or ketone) and phosphorous acid or derivative thereof. [See the procedure of Moeoritzer and Irani, *J. Org. Chem.*, 31, 1603 (1966).]

Preferred chelating agents for use with the linkers of the present invention are PA-DOTA and AL-DOTA.

The amide bond between the linker and effector moiety should be formed under mild conditions that do not affect protein structure. At the same timer the linkage should be strong and stable under neutral (serum) conditions and yet be rapidly cleaved under mild acidic conditions such as those present in the cell under certain metabolic conditions, for example acidic conditions (pH 4.5 to 5.5) present in all lysosomes. Since the cleavage site is at the bond between the amino group of the amino-group-containing substance and the remainder of the compound, the substance is released intact, with no additional component and with no deletions.

The linker and amine-containing effector moiety are reacted at about a 1 to 1 stoichiometry, or with a slight excess of linker present. As the anhydride moiety of the linker is much more reactive than the isothiocyanate moiety, a 1 to 1 stoichiometry of linker to effector moiety results in substantially all the effector moiety being bound to the linker by the anhydride functionality. When the effector moiety contains a chelating agent, an organic solvent in which the chelating agent is soluble is preferably used as the reaction solvent. Examples of such solvents include 2,2,2-trifloroethanol dimethylformamide and dimethyl sulfoxide.

The radionuclides can be complexed with the chelating agent prior to joining the chelating agent to the linker or after joining the chelating agent to the linker. Alternatively, the chelate is formed after formation of the amide bond between the linker and chelating agent. Preferably, the radionuclide is complexed with the chelating agent after the chelating agent and target directing moiety have been bound to the linker. Chelates form readily upon mixing in an aqueous solution at a pH of about 5 to about 8. Preferably, the reaction is carried out in a medium having a pH of about 6 to about 8, and more preferably about 7 to about 8. Ambient temperatures of about 10° C. to 40° C. can be readily employed for metal ion chelation. The amount of metal ion employed may be from trace amounts to an amount in excess of equimolar with the chelating agent. Preferably, the formation of the chelate occurs at room temperature, between about 15° C. to about 25° C.

In accordance with the present invention, conjugates comprising an effector moiety attached to a cleavable linker which in turn is attached to a targeting protein are administered to a human or mammalian host for diagnostic or therapeutic purposes, depending on the effector moiety. The conjugate may be administered intravenously, intraperitoneally, intralyphatically, locally, or by other suitable means, depending on such factors as the type of target site. The amount to be administered will vary according to such factors as the type of effector moiety and the affinity of the targeting protein for the target site of interest. Appropriate dosages may be established by conventional procedures, e.g., animal studies and human clinical trial.

The invention will be further clarified by a consideration of the following examples, which are intended to be purely exemplary of the present invention.

EXAMPLES

EXAMPLE 1

4-Isothiocyanatophthalic Anhydride (ACL-3)

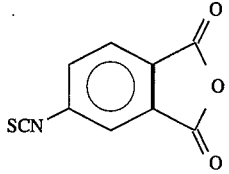   I

To a slurry of 4-aminophthalic acid (2.7183 grams(g), 15.00 mmol) and anhydrous potassium carbonate (8.75 g, 63.3 mmol) in 70 mL of tetrahydrofuran (THF) was added thiophosgene (2.30 mL, 30.18 mmol). The reaction mixture was stirred 10 minutes at ambient temperature, then heated to reflux for one hour. After cooling to room temperature, the reaction product solution was filtered through celite and then concentrated to dryness under a stream of dry nitrogen and under an efficient fume hood to avoid exposure to thiophosgene. The crude 4-isothiocyanatophthalic acid was thus recovered; 1H NMR (300 MHz, acetone-d6) d 10.22 (br s, 2H), 7.81 (br s, 1H) 7.61 (s,1H), 7.48 (br s, 1H); 13C NMR (75 MHz, acetone-d6) d 167.8, 167.7, 138.3, 135.8, 134.4, 131.7, 131.7, 128.6, 126.5.

The 4-isothiocyanatophthalic acid thus obtained was immediately heated to reflux in a mixture of trifluoroacetic anhydride and methylene chloride for 2 hours under a nitrogen atmosphere. After cooling to room temperature, the reaction mixture was concentrated under reduced pressure. Recrystallization of the resultant solid from 30 mL of carbon tetrachloride afforded 4-isothiocyanatophthalic anhydride as brownish-purple crystals in a yield of 2.3778 g, (77 percent of theoretical). The title compound melted at 106°–108° C.; 1H NMR (300 MHz, acetone-d6) d, 8.15 (d, J=8.1 Hz, 1H), 8.06 (d, J=1.7 Hz, 1H), 7.97 (dd, J=8.1, 1.7 Hz, 1H); 13C NMR (75 MHz, acetone-d6) d 163.3, 162.6, 139.8, 134.8, 134.6, 130.6, 128.2, 123.5, 111.6; IR (CHCl₃) 2010 (br), 1840, 1740 cm-1; MS m/e 205, 161, 133 (base), 74.

EXAMPLE 2

2-(4'-(Isothiocyanato)thiophenoxy) Maleic Anhydride (ACL-1)

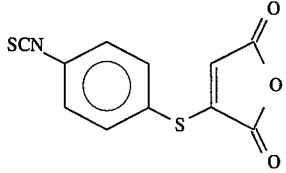   II

To a solution of 70 percent epoxysuccinic acid, disodium salt (6.573 g, 26 14 mmol) in 25 mL water was added a filtered solution of 4-aminothiophenol (3.251 g, 25.97 mmol) in aq NaOH (28 mmol in 20 mL of water) via polyethylene cannula under nitrogen with stirring. After 22 hours, the cloudy reaction mixture was washed with 30 mL of ether and then acidified to pH 3 with 6M HCl, (13.3 mL, 79.8 mmol) producing a white solid precipitate. The solid was washed with 20 mL of water and dried (70° C., 0.05 mm Hg vacuum) to afford 3.364 g, (50 percent of theoretical) of 2-[4'-(amino)thiophenoxy]-3-hydroxymaleic acid; 1H NMR (DMSO-d6, d) 8.1 (2H, br), 7.13 (2H, d, J=8.3 Hz), 6.48 (2H, d, J=8.3 Hz), 4.05 (2H, d, J=7.6 Hz), 3.47 (2H, d, J=7.6 Hz); 13C NMR (DMSO-d6, d) 173.1, 171.3, 149.4, 136.0, 116.2, 114.1, 70.4, 56.0; IR (Nujol mull, cm-1) 3410 (br, m), 1710 (br, m).

To a slurry of 2-[4'-(amino)thiophenoxy]-3-hydroxymaleic acid (0.370 g, 1.438 mmol) and freshly powdered, freshly dried K₂CO₃ (1.217 g, 8.806 mmol in THF (30 mL) under nitrogen was added thiophosgene (0.33 mL, 0.498 g, 4.33 mmol). The reaction mixture was stirred vigorously at room temperature for 1 hour, then at reflux for 30 minutes. Upon cooling to room temperature, the reaction mixture was filtered and the solvent evaporated off to afford crude 2-[4'-(isothiocyanato)-thiophenoxy]-3-hydroxymaleic acid as an orange oil; (This material was used directly in the next step but could be crystallized from CHCl₃) MP 156°–158° C. with decomposition; 1H NMR (acetone-d6, d) 10.2 (2H, br), 7.58 (2H, d, J=8.8 Hz), 7.32 (2H, d, J=8.8 Hz), 4.99 (1H, br s), 4.79 (1H, d, J=4.8 Hz), 4.26 (1H, d, J=4.8 Hz); 13C NMR (acetone-d6, d) 172.7, 171.0, 135.7, 133.7, 130.9, 127.1, 127.0, 71.7, 55.7; IR (Nujol mull, cm-1) 3390 (br, m), 2040 (s), 1730 (s), 1695 (s); mass spectrum, m/e 299, 263, 191, 166, 108, 57 (base).

The 2-[4'-(Isothio-cyanato)thiophenoxy]-3-hydroxymaleic acid (4.510 g, 15.07 mmol) was slurried in 140 mL of CHCl₃ under nitrogen, treated with trifluoroacetic anhydride (5.30 mL, 7.88 g, 37.5 mmol), and heated to reflux. After 6.5 hours, the homogeneous reaction mixture was allowed to cool to room temperature, concentrated, taken up in hot CCl₄ (80 mL), filtered hot, concentrated to one third volume, and diluted with 10 mL of hexane. Crystallization occurred upon standing at room temperature over 30 minutes. After storing at 0° C. an additional 2 hours, the light orange crystals of 2-[4'-(isothiocyanato)thiophenoxy] maleic anhydride (the titled compound) were collected by filtration, washed twice with 30 mL portions of hexane and dried overnight under vacuum (0.05 mm Hg).

The titled product was recovered in a yield of 3.597 g, (91 percent of theoretical) and melted at 114°–116° C.; 1H NMR (CDCl₃, d) 7.58 (2H, d, J=8.4 Hz), 7.36 (2H, d, J=8.4 Hz), 5.94 (1H, s); 13C NMR (CDCl₃, d) 161.9, 155.0, 139.1, 135.5, 134.8, 127.7, 124.8, 122.1, 120.5; IR (Nujol mull, cm-1) 2100 (s), 1820 (m), 1740 (s); mass spectrum, m/e 263 (base), 191, 149.

EXAMPLE 3

7-Oxabicyclo[2.2.1]hept-5-ene-5-isothiocyanatomethyl-cis-2,3-dicarboxylic Anhydride (ACL-2)

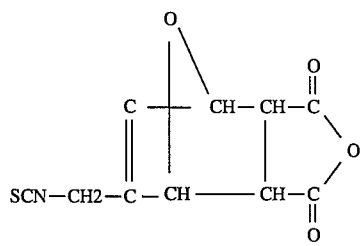   III

To 3-furoic acid (7.513 g, 67.02 mmol) was added thionyl chloride (7.5 mL, 102.8 mmol). The mixture was heated gradually to reflux; the reaction vessel was teed to a water aspirator to absorb HCl as it was liberated; the remaining arm of the tee was left open to the atmosphere. After 1 hour at reflux, the reaction mixture was concentrated under reduced pressure (20° C., 20 mm Hg). The crude product was purified by distillation to afford 3-furoyl chloride as a clear, colorless liquid in a yield of 8.796 g, (100 percent of theoretical) having a boiling point of 47°–48° C. at 20 mm Hg; 1H NMR (300 MHz, CDCl$_3$) d 8.21 (s, 1H), 7.50 (s, 1H), 6.78 (s, 1H); 13C NMR (75 MHz, CDCl$_3$) d 160.2, 152.1, 145.3, 124.6, 109.8; IR (neat) 1755 cm-1; MS m/e 130, 95 (base), 67.

The 3-furoyl chloride (9.23 g, 70.7 mL) was added dropwise with vigorous stirring over 15 minutes to a concentrated ammonium hydroxide solution (29 percent) (100 mL, 1480 mmol) at 0° C. while maintaining the temperature between 0°–5° C. After the addition, the reaction mixture was stirred another 10 min at 5° C. and then another 10 min at 0° C. and then allowed to warm to ambient temperature over 1.5 hour period. Excess ammonia and water were removed under reduced pressure. The residual material was partitioned in a mixture composed of ethyl acetate (100 mL), n-butanol (50 mL), saturated NaCl (50 mL) and water (25 mL). The phases were separated and the aqueous layer extracted with 50 mL of n-butanol. The combined organic solutions were washed twice with 25 mL portions of saturated NaCl, dried over anhydrous MgSO$_4$, filtered and the solvent evaporated off.

The crude amide product was taken up in boiling ethyl acetate (150 mL), filtered hot, diluted with toluene (150 mL) and concentrated on a hot plate to approximately 20 mL of total volume, at which point the solution became cloudy. Gradual cooling to ambient temperature, followed by overnight storage at 0° C. afforded colorless crystals of furan-3-carboxamide (5.873 g, 75 percent of theoretical): m.p. 172°–174° C.; 1H NMR (300 MHz, DMSO-d6) d 8.14 (s, 1H), 7.68 (s, 1H), 7.62 (br s, 1H), 7.16 (br s, 1H), 6.79 (s, 1H), 13C NMR (75 MHz, DMSO-d6) d 163.4, 145.2, 143.9, 122.9, 109.3; IR (Nujol) 3340, 3160, 1660, 1610 cm-1; MS m/e 111, 95 (base), 67, 44.

| Analysis: | percent | | |
|---|---|---|---|
| | C | H | N |
| Calc. for C$_5$H$_5$NO$_2$: | 54.06 | 4.54 | 12.61 |
| Found: | 53.94 | 4.51 | 12.98 |

Lithium aluminum hydride (1.247 g, 32.86 mmol) was slurried in THF (20 mL) under nitrogen and heated to reflux. To the refluxing mixture was added a solution of furan-3-carboxamide (2.89 g, 26.0 mmol) in THF (90 mL) in small portions over 1 hour. When the addition was complete, the reaction mixture was refluxed another 1 hour and then allowed to cool to ambient temperature. Excess LiAlH$_4$ was destroyed by cautious addition of water (3.0 mL). The resulting thick olive-green solution was treated with 5M NaOH (40 mL) and diluted with water (260 mL). After filtration through celite, the aqueous mixture was extracted thrice with 50 mL portions of ether and the combined ether solutions were dried over anhydrous MgSO$_4$, filtered, and distilled at atmospheric pressure to remove the ether and THF. 3-(Aminomethyl)furan was isolated by fractional distillation under reduced pressure and recovered in a yield of 0.572 g, (23 percent of theoretical, unoptimized): b.p. 72°–73° C./20 mm Hg; 1H NMR (300 MHz, CDCl$_3$) d 7.36 (s, 1H), 7.32 (s, 1H), 6.36 (s, 1H), 3.71 (s, 2H), 1.34 (br s, 2H); 13C NMR (75 MHz, CDCl$_3$) d 143.2, 138.9, 127.3, 109.8, 37.4; IR (neat) 3370, 1580 cm-1; MS m/e 97, 81, 69 (base).

To a solution of 3-(aminomethyl)furan (0.565 g, 5.818 mmol) in 10 mL of CHCl$_3$ at 0° C. was added 10 mL of a saturated NaHCO$_3$ solution and thiophosgene (0.66 mL, 8.66 mmol). The reaction mixture was stirred vigorously for 45 min while maintaining the temperature at between 0°–5° C. The phases were then separated and the aqueous layer extracted with CHCl$_3$ (10 mL). The combined organic solutions were dried (MgSO$_4$), filtered, and the volatiles removed by blowing a gentle stream of nitrogen over the solution. Traces of residual solvent and thiophosgene were then evaporated off under high vacuum (20° C./0.05 mm Hg) to afford 0.659 g,(81 percent of theoretical) of 3-(isothiocyanatomethyl)furan as a dark orange liquid which was found to be pure by NMR and suitable for use in the Diels-Alder step: 1H NMR (300 MHz, CDCl$_3$) d 7.45 (s, 1H), 7.42 (s, 1H), 6.42 (s, 1H), 4.54 (s, 2H); 13C NMR (75 MHz, CDCl$_3$) d 144.0, 139.9, 132.7, 119.5, 109.4, 40.2; IR (neat) 2090, 1595 cm-1; MS m/e 139, 81 (base).

3-(Isothiocyanatomethyl)furan (0.659 g, 4.734 mmol) and maleic anhydride (0.475 g, 4.844 mmol) were dissolved in ether (17 mL) and stirred at room temperature for 16 hours under a positive pressure. The reaction mixture evaporated to dryness overnight leaving a light colored solid. The solid was triturated with ether (3.0 mL), collected by filtration, washed with ether (8×1.0 mL), and dried to afford the title 4-isothiocyanatophthalic anhydride as off-white crystals in a yield of 0.842 g, (75 percent of theoretical) which melted at 128°–129° C.; 1H NMR (300 MHz, acetone-d6) d 6.58 (br s, 1H), 5.41 (s, 1H), 5.35 (s, 1H), 4.71 (AB q, J=18.4 Hz, 2H), 3.61 (d, J=6.8 Hz, 1H), 3.51 (d, J=6.8 Hz, 1H), 13C NMR (75 MHz, acetone-d6) d 172.1, 172.0, 147.4, 133.6, 128.9, 84.1, 83.5, 51.0 49.7, 43.0; IR (Nujol) 2210, 2135, 1850, 1780, 1760 cm-1; MS m/e 237, 209, 179, 139, 98, 81 (base), 53.

| Analysis: | percent | | |
|---|---|---|---|
| | C | H | N |
| Calc. for C$_{10}$H$_7$NO$_4$: | 50.63 | 2.97 | 5.90 |
| Found: | 50.33 | 2.97 | 6.01 |

EXAMPLE 4

Preparation of Derivatives of ACL-3 and Their Hydrolytic Cleavage Rates

To a solution of 4-isothiocyanatophthalic anhydride (0.065 g, 0.3168 mmol) in a mixture of THF (0.5 mL) and ether (1.0 mL) was added aniline (28.0 µL, 0.307 mmol). After stirring 30 min, the reaction mixture was concentrated to approximately 0.5 mL under a stream of nitrogen and added dropwise to fresh ether (3.0 mL) to induce partial crystallization. The ether solution was then chilled to 2° C. in an open vessel. Over a period of 4 days, the ether evaporated to afford dark orange crystals of the isosthiocyanate-acid-amide in a yield of 0.085 g, (93 percent of theoretical). NMR shows the product to be a 3:1 mixture of regioisomers: IR (THF) 3260 (br), 2085 (br), 1740, 1635 cm-1; MS m/e 280 (M-H$_2$O), 236, 205, 161, 133, 93, 64 (base).

To a solution of this thus prepared isothiocyanate-acid-amide (0.080 g, 0.268 mmol) in THF (3.0 mL) was added n-propylamine (22.0 µL, 0.268 mmol). After stirring 18 hours under a nitrogen atmosphere, the reaction mixture was concentrated under a stream of dry nitrogen to one-third the original volume and added dropwise to fresh ether (12 mL) to induce precipitation. The off-white solid formed was collected by filtration, washed twice with 2.0 mL portions of additional ether and dried to afford 0.046 grams of the thiourea-acid-amide (48 percent of theoretical). NMR indicates a mixture of two regioisomers: IR (THF) 3475 (br), 3265 (br), 1705 cm-1; MS m/e 357, 339, 320, 264, 238, 175, 162, 119, 93 (base).

| HALF-LIFE OF ISOMERS IN AQUEOUS MEDIA TIME AT GIVEN TEMPERATURE | | | |
|---|---|---|---|
| Temperature °C. | pH | Major isomer | Minor isomer |
| 22 | 1.4 | 49 m | 57 m |
| " | 2.2 | 77 m | 89 m |
| " | 3.2 | 103 m | 119 m |
| " | 4.0 | 5.5 h | 7 h |
| " | 4.9 | 62 h | 28 d |
| " | 6.0 | 16 d | 28 d |
| " | 7.1 | 79 d | 205 d |
| " | 8.0 | S | S |
| 37 | 1.4 | 10 m | 11 m |
| " | 2.2 | 15 m | 15 m |
| " | 3.2 | 26 m | 29 m |
| " | 4.0 | 80 m | 128 m |
| " | 4.9 | 6.7 h | 9.1 h |
| " | 6.0 | 2.9 d | 4.5 d |
| " | 7.1 | 15 d | 22 d |
| " | 8.0 | 40 d | 45 d | m = minutes: h = hours; d = days; S = stable within the limits of detection of the experiment.

EXAMPLE 5

Preparation of Derivatives of ACL-1 and Their Hydrolytic Cleavage Rates

To a solution of 2[-4'-(isothiocyanato)thiophenoxy]maleic anhydride (1.748 g, 6.639 mmol) (Example II) in ether (90 mL) was added aniline (0.61 mL, 0.62 g, 6.69 mmol), with stirring. A very mild exotherm was observed. Product began to crystallize from the reaction mixture within 10 minutes. After stirring 15 hours under nitrogens the reaction mixture was stored at 0° C. for 3 hours to complete crystallization. The chilled reaction mixture was filtered and the solid which was collected was washed twice with 10 mL portions of hexane and dried (0.05 mm Hg vacuums 4 hours) to afford 1.574 g of the isothiocyanate-acid-amide (67 percent of theoretical) which melted at 162°–164° C.; 1H NMR (DMSO-d6, d) 10.11 (1H, s), 7.62 (2H, d, J=8.6 Hz), 7.58–7.47 (5H, m), 7.28 (2H, br t, J=7.4 Hz), 7.04 (1H, 7.4 Hz), 5.98 (1H, s); 13C NMR (DMSO-d6, d) 165.6, 160.9, 144.9, 138.7, 135.7, 135.4, 131.5, 128.7, 128.2, 127.2, 123.6, 120.1, 119.2; IR (Nujol mull, cm-1) 3320 (br m), 2070 (s), 1680 (s); mass spectrum, m/e 356, 263 (base), 191.

The above isothiocyanate-acid-amide (0.326 g, 0.9147 mmol) was slurried in acetonitrile (100 mL) and then treated with n-propylamine (75 µL, 0.054 g, 0.91 mmol). After stirring 30 minutes under nitrogen, the reaction solution was diluted with THF (15 mL), for improved solubility, and another portion of n-propylamine (75 µL) was added. The reaction mixture was evaporated to dryness using an aspirator 20 minutes after the second amine addition. The resulting white solid was partitioned between ethylacetate (50 mL), THF (80 mL), and saturated NH4Cl (30 mL). The phases were separated; the organic layer was washed with saturated NH4Cl (3×30 mL) and saturated NaCl (30 mL), then dried (MgSO4), filtered, and concentrated (aspirator, then 0.05 mm Hg vacuum overnight) to afford the desired thiourea-acid-amide (0.257 g, 68 percent of theoretical): 1H NMR (acetone-d6, d) 10.79 (1H, br s), 9.90 (1H, br s), 8.60–7.40 (11H, m), 6.21 (1H, s), 4.16–3.87 (2H, m), 2.57–2.42 (2H, m), 1.36 (3H, t6, J=6.3 Hz); IR (Nujol mull, cm-1) 3300 (br), 1580 (s). In aqueous media at 22° C. this derivative has a half-life of 57 minutes at pH 1.2, 80 minutes at pH 2.3, 172 minutes at pH 3.6, 12 hours at pH 4.9, 18 hours at pH 6.1, 21.5 hours at pH 6.8, 20 hours at pH 7.8, and 16 hours at pH 8.8. In aqueous media at 37° C. this derivative has a half-life of 34 minutes at pH 3.6, and 6 hours at pH 7.8.

EXAMPLE 6

Preparation of Derivatives of ACL-2 and Their Hydrolytic Cleavage Rates

The compound of Example 3 (ACL-2) (0.122 g, 0.514 mmol) and phenethylamine (64 µL, 0.510 mmol) were dissolved in THF (2.0 mL). After stirring 40 minutes under flow-through nitrogen, approximately two-thirds of the solvent had evaporated off with concomitant formation of an off-white precipitate. The reaction mixture was diluted with ether (3.0 mL) and stirred vigorously for 5 minutes. The acid-amide product was isolated by filtration, washed with ether (2×1.0 mL), and dried to recover the product in a yield of 0.159 g, (87 percent of theoretical). NMR supports the indicated structure as a 55:45 mixture of regioisomers: IR (Nujol) 3340, 2190, 2100, 1725 cm-1; MS m/e 374, 358, 322, 277, 231, 202, 160, 104 (base), 91, 81.

To a solution of the isothiocyanate-acid-amide (0.054 g, 0.151 mmol) in THF (15 mL) was added n-propylamine (12.5 µL, 0.149 mmol). The reaction mixture was stirred 5 hours under nitrogen and then evaporated to dryness. The resultant dark yellow oil was re-dissolved in THF (1.0 mL) and added dropwise to stirred ether (20 ML) to induce precipitation. The white solid thus formed was collected by filtration, washed with fresh ether (2.0 mL), and dried to afford thiourea-acid-amide derivative in a yield of 0.048 g, (77 percent of theoretical). NMR supports the indicated structure with approximately the same regioisomer ratio present in the starting isothiocyanate: IR (Nujol) 3290, 1655, 1645 cm-1. In aqueous media at pH 4.0 and 37° C. the hydrolytic half-life is about 3 days.

EXAMPLE 7

Preparation OF AL-DOTA

Phthalic anhydride (14.8 g, 100 mmol), γ-aminobutyric acid (10.3 g, 100 mmol), 1.3 mL of triethylamine and 150 mL of toluene were placed in a round-bottom flask equipped with a Dean-Stark trap and water condensor. The mixture was brought to reflux and water was removed azeotropically over a 1.5 hour period (1.75 mL obtained versus 1.8 mL theoretical). The solution was allowed to cool and stand overnight and the resulting white crystals were filtered, washed with hexane and dried. The crude crystals were then washed withd 250 mL of 5 percent aqueous hydrochloric acid and 100 mL of cold water. Drying afforded 4-(N-phthalimido)butanoic acid in a yield of 19.0 g, (81.5 mmol; 82 percent of theoretical). The product was recrystallized from 30 percent methanol in water and melted at 114.5°–115.5° C.: $^1$H NMR (CDCl$_3$) δ7.84 (dd, 2H, J$_1$=J$_2$= 3.0 Hz), 7.72 (dd, 2H, J$_1$=J$_2$=3.0 Hz), 6.05 (broad s, 1H), 3.77 (t, 2H, J=6.8 Hz), 2.42 (t, 2H, J=6.8 Hz), 2.02 (p, 2H, J=6.8 Hz); $^{13}$C NMR (CDCl$_3$) δ177.9, 169.4, 134.0, 123.3, 37.1, 31.2, 23.6;

| Analysis: | percent | | |
|---|---|---|---|
| | C | H | N |
| Calc. for $C_{10}H_7NO_4$: | 50.63 | 2.97 | 5.90 |
| Found: | 50.33 | 2.97 | 6.01 |

AnaL. CALCD, FOR $C_{12}H_{11}NO_4$: C, 61.80; H, 4.75; N, 6.01; Found: C, 61.64; H, 4.72; N, 5.98.

D,1-2-Bromo-4-(N-phthalimido)butanoic acid isopropyl ester was prepared from 4-(N-phthalimido)butanoic acid using the same procedure which was used for the synthesis of d, 1-2-bromo-4-(4-nitrophenyl)butanoic acid isopropyl ester and was obtained in 68 percent yield as a white solid which melted at 72°–74.5° C.) after a flash silica gel chromatography step using chloroform as the eluent ($R_f$= 0.38, chloroform): $^1$H NMR (CDCl$_3$) δ7.85 (dd, 2H, J$_1$=J$_2$= 2.8 Hz), 5.04 (septet, $^1$H, J=6.2 Hz), 4.23 (dd, 1H, J$_1$=J$_2$=6.9 Hz), 3.85 (dt, 2H J$_1$=6.6 Hz, J$_2$=2.4 Hz), 2.51 (m, 1H), 2.36 (m, 1H), 1.29 (d, 3H, J=3.9 Hz), 1.26 (d, 3H, J=3.9 Hz); $^{13}$C NMR (CDCl$_3$) δ168.5, 168.0 134.0, 132.9, 123.3, 69.9, 42.9, 35.8, 33.5, 21.4, 21.3;

| Analysis: | percent | | |
|---|---|---|---|
| | C | H | N |
| Calc. for $C_{15}H_{16}NO_4Br$: | 50.99 | 4.57 | 3.97 |
| Found: | 50.64 | 4.57 | 3.87 |

To a stirred solution of cyclen (1,4,7,10-tetraazycyclododecane) free base (2.00 g, 11.6 mmol, FW=172.28) in 40 mL of pentene stabilized chloroform was added d,1-2-bromo-4-(N-phthalimido)butanoic acid: isopropyl ester (3.50 g, 10.00 mmol) under a nitrogen atmosphere with stirring. The reaction solution was stirred for 48 hours at a room temperature of 25° C. TLC analysis (12:4:1-SS2) revealed conversion to the monoalkylation product ($R_f$=0.57 ninhydrin, iodine, and UV active versus a minor, high $R_f$=0.71). The yellow chloroform solution was applied to a 2"×12" flash silica gel column which had been pre-eluted with 5 percent methanol in chloroform. The oil was then eluted with this solvent (500 mL) and then solvent system 1 [40 percent chloroform/40 percent methanol/20 percent concentrated ammonium hydroxide (v/v/v)] was applied.

The minor, rapidly eluting component (bis alkylation adduct-190 mg) was separated from the major UV active product 1,4,7,10-tetraaza-1-N-(1-carboisopropoxy)-3-[(N-phthalimido)propyl]cyclododecane: monohydrobromide salt which was obtained as a white glass in a yield of 4.22 g (8.01 mmol, 81 percent of theoretical). The ammounium hydroxide in the solvent system was removed with an efficient vacuum to avoid phthalamide hydrolysis.

$^1$H NMR (CDCl$_3$) δ 7.89 (m, 2H), 7.75 (m, 2H), 5.01 (sextet, ]H, J=6.2 Hz), 3.95 (m, 1H), 3.81 (m, 1H), 3.34 (dd, 1H, J$_1$=11.6 Hz, J$_2$=3.7 Hz), 2.85–3.1 (m, 16H), 2.12 (m, 1H), 1.93 (m, 1H), 1.24 (d, 3H, J=6.2 Hz), 1.23 (d, 3H, J=6.2 Hz); $^{13}$C NMR (CDCl$_3$) δ168.4, 134.2, 131.9, 123.3, 68.7, 62.9, 49.1, 48.5, 47.0, 45.3, 35.1, 28.3, 22.0, 21.9; IR (CDCl$_3$ film on NaCl plates) cm$^{-1}$ 2980, 2940, 2845, 1765, 1705, 1395, 1105; MS (FAB in dithioerthyritol/dithiothreitol ("Magic Bullet") matrix) m/e (1 percent) 446 (100 percent, (M+H+), 464 (5 percent, (M+H)$^+$ for phthalamic acid impurity); Negative ion mode 606, 608 (6 percent, (M+2Br–H)–), 462 (10 percent, (M–H)$^-$ for maleamic acid impurity), 445 (20 percent, (M)$^-$), 79, 81 (100 percent, Br$^-$);

| Analysis: | percent | | |
|---|---|---|---|
| | C | H | N |
| Calc. for $C_{10}H_7NO_4$: | 50.63 | 2.97 | 5.90 |
| Found: | 50.33 | 2.97 | 6.01 |

Anal. Calcd. for $C_{23}H_{35}N_5O_4$·HBr: C, 52.47; H, 6.89; N, 13.30; Found: C, 52.06; H, 6.70; N, 13.67.

1,4,7,10-Tetraaza-1-N-(1-carboisopropoxy)-3-[(N-phthalimido)propyl]cyclododecane: monohydrobromide salt (457 mg, 0.87 mmol, FW=526.1 mono HBr salt) was dissolved in 10 mL of dry acetonitrile under nitrogen and anhydrous potassium carbonate (481 mg, 3.49 mmole) was added with stirring. To this slurry was added benzylbromoacetate (752 mg, 3.28 mmol) and the mixture was stirred vigorously for 48 hours. The slurry was filtered and the solvent evaporated off to give a light yellow oil which was redissolved in a minimum amount of chloroform and applied to a 1"×7" flash silica gel column which had been pre-eluted with 5 percent ethanol in chloroform. Elution with this solvent afforded a rapidly moving, yellow oil (146 mg; $R_f$=0.96 in SS1) which was not characterized. Upon elution of this band, solvent system 1 was applied which eluted a second UV-active fraction (250 mg) followed by a third fraction of the sodium bromide salt of 1,4,7,10-Tetraaza-1-N-(1-carboisopropoxy)-3-[(N-phthalimido)propyl]-tris-4, 7,10 -N,N,N-[(1-carboxybenzyl) methyl]cyclododecane (360 mg, 0.36 mmol, FW=992 for NaBr ionophore; $R_f$=0.6 in solvent system 1; $R_f$=0.10 in 10 percent ethanol in chloroform):

$^1$H (DMSO d6 at 100° C.) δ 7.81 (s, 4H), 7.33 (m, 15H), 5.12 (m, 6H), 4.86 (sextet, 1H, J=6.3 Hz), 3.74 (t, 2H, J=6.0 Hz), 3.45 (m, 6H), 3.2 (m, 4H), 2.3–2.9 (m, 16H), 1.94 (m, 2H), 1.16 (d, 3H, J=6.3 Hz), 1.15 (d, 3H, J=6.3 Hz); $^{13}$C NMR (DMSO d6 at 100° C.) δ 171.4 (broad s), 167.3, 135.6, 133.8, 131.3, 127.8, 127.5, 127.3, 125.9, 122.367.9, 65.3, 60.4 (broad s), 55.7, 54.7, 54.6, 51.0 (broad s), 47.1, (broad s), 36.0, 20.9, 17.8; IR (CDCl$_3$ film on NaCl plates) cm$^{-1}$ 3040, 2950, 1770 (shoulder), 1725, 1705, 1590, 1450, 1390, 1360; MS (FAB in "magic bullet" matrix) m/e (1 percent) 912 (45 percent, (M+Na)$^+$), 23 (100 percent, Na+).

1,4,7,10-Tetraaza-1-N-(1-carboisopropoxy)-3-[(N-phthalimido)propyl]-tris 4,7,10-N,N,N-[(1-carboxybenzyl)methyl]cyclododecane (3.8 g, 3.83 mmol, FW=992) was dissolved in 45 mL of a 50:50 solution of ethanol and 6N hydrochloric acid under a nitrogen atmosphere and palladium catalyst (1.00 g 10 percent on carbon) was added. Hydrogen gas was purged through the solution for 18 hours with stirring. The solution was then filtered through a pad of celite and the solvent was removed in vacuo. The resulting glassy solid was dissolved in 150 mL of 9N hydrochloric acid and refluxed overnight. Upon cooling phthalic acid precipitated from the acidic medium. The solvent was removed and the crude white solid which remained was dissolved in 10 mL of water. This solution was extracted with 6 times with 10 mL portions of ether using a microextracter apparatus (Mixxor™) and the combined ether fractions were dried over magnesium sulfate, filtered and evaporated to provide crystalline phthalic acid (630 mg, 3.79 mmol) in quantitative yield based upon starting material. The aqueous portion was evaporated and vacuum dried overnight to provide the trishydrochloride.NaCl salt of 1,4, 7,10-tetraaza-1-N-(1-carboxy-3-aminopropyl)-tris-4,7,10- N,N,N-(1-carboxymethyl)cyclododecane (Al-DOTA, in a yield of 2.1 g, (3.42 mmol) 89 percent of theoretical: $R_f$=0.12 in solvent system 2) [chloroform/methanol/concentrated ammounium hydroxide, 12/4/1 (v/v/v)]:

¹H NMR (D₂O with dioxane internal standard, pH=1.0, 90° C.) δ 4.15 (m, 4H, ), 3.1–3.8 (m, 21H); 2.20 (m, 1H), 2.03 (m, 1H) ¹³C NMR (D₂O with dioxane internal standard, pH=1.0, 90° C.) δ 176.1, 175.0, 171.5, 69.0 (dioxane), 60.8, 57.7, 55.7, 54.0, 53.4, 51.9, 40.3, 40.0, 28.3; MS (FAB in "magic bullet" matrix) m/e (1 percent) 448 (100 percent, (M+H)⁺), 470 (M+Na)⁺; HRMS Calculated for $C_{18}H_{33}N_5O_8$+Na(M+Na)⁺: 470.2227; Found: 470.2215.

EXAMPLE 8

Preparation of ACL-2-AL-DOTA

THE compound of Example 3 (ACL-2) (0.066 g, 0.278 mmol), Al-DOTA.3HCl (0.153 g, 0.275 mmol), 2,2,2-trifluoroethanol (20 mL), and 2,6-lutidine (96 mL, 0.824 mmol) were stirred under nitrogen for 5 hours. The homogeneous solution was then added dropwise to ether (40 mL) and the resultant ether solution was then added to hexane (50 mL). The hygroscopic precipitate formed was collected by filtration and dried and recovered in a yield of 0.192 g, (100 percent of theoretical). HPLC analysis of the thus recovered solid supports the structure of the Al-DOTA-amide-acid derivative of the invention as a mixture of two regioisomers: MS (FAB) m/e 685 (positive ion M+H).

Different derivatives of the invention are expected to have similar pH/stability profiles as long as the first amine added to the compounds of the invention has an aromatic group on it.

EXAMPLE 9

Preparation and Stability of Conjugates Using the Linker ACL-2

9A Preparation of ACL-2-Ala-PA-DOTA ¹⁷⁷Lu

PA-DOTA (0.069 g) was dissolved in water (3.5 mL) and the pH adjusted to 8.75 by the addition of triethylamine (0.085 mL). The PA-DOTA solution was then diluted with THF (3.5 mL). BOC-L-alanylanhydirde (0.045 g) was added to the diluted solution and the reaction mixture was stirred at room temperature. After 30 minutes the reaction was further diluted with acetonitrile (50 mL) and immediately concentrated to dryness under reduced pressure. The residue was triturated once with ether (25 mL) and twice with THF (25 mL) to afford BOC-Ala-PA-DOTA.

Crude BOC-Ala-PA-DOTA from above was dissolved in trifluoroacetic acid (3.5 mL) and immediately evaporated to dryness under a stream of dry nitrogen. The solid residue was triturated twice with ether (15 mL) and twice with THF (15 mL) to give L-Ala-PA-DOTA (0.066 g: MF (FAB) m/e 617 (positive ion M+Na).

The ACL-2-Ala-PA-DOTA complex was formed by reacting Ala-PA-DOTA (0.024 g, 0.0404 mmoles) with ACL-2 (0.0662, 0.278 mmoles) in 2,2,2,-trifluoroethanol (20 mL) and 2,6-lutidine (96 μL, 0.824 mmols as described in Example 8 for AL-DOTA. To 8 μL (5 mM) of the linker-chelating agent (ACL-2-Ala-PA-DOTA) was added 40 μL of ¹⁷⁷Lu (1 mM in 0.05 in HCl), which was mixed on a vortex mixer. To the mixture was added 50 μL of a HEPES buffer (N-2-hydroxyethylpiperazine-N'-2-ethane-sulfonic acid, 1.0 M; pH 7.0), and again mixed. The ACL-2-Ala-PA-DOTA-¹⁷⁷Lu was subsequently purified on a reversed phase cartridge (PRP of Alltech). The fraction which came off with a 2:1 acetonitrile carbonate (50 mM; pH 9.5) solvent mixture accounted for 48 percent of the ¹⁷⁷Lu activity and was identified as the ACL-2-Ala-PA-DOTA-¹⁷⁷Lu complex by HPLC analysis. This fraction was used for the subsequent conjugation with the IgG or F(ab')₂ of the MAb CC49.

9B Preparation of ACL-2-Al-DOTA ¹⁷⁷Lu

The ACL-2-Al-DOTA ¹⁷⁷Lu complex was prepared and purified in the same manner as that described in Example 9A, and obtained in approximately 14 percent yield based on the activity of ¹⁷⁷Lu. The fraction which came off in a 2:1 acetonitrile-carbonate (50 mM; pH 9.5) solvent mixture was used for conjugation with the IgG or F(ab')₂ of the MAb CC49.

9C Preparation of ACL-2-Ala-PA-DOTA ¹⁷⁷Lu F(ab')2 CC49)

Whole IgG CC49 was derived as described in published PCT Application WO 89/00692 and Published PCT Application WO 90/04410. F(ab')₂ CC49 was prepared by enzymatic digestion of IgG CC49 according to the procedures described by Lamoyi and Nisonoff, *J. Immunol. Methods*, 56:235–243 (1983) The F(ab')₂ fragments were exchanged into a carbonate buffer (50 mM, pH 9.5) and concentrated to approximately 16 mg/mL.

The ACL-2-Ala-PA-DOTA-¹⁷⁷Lu from Example 9A (12.8 n moles) in 50 μL was evaporated under nitrogen for 5 minutes. To this was then added 150 μL of the F(ab')2 (26.8×10⁻¹¹ moles/μL) in a carbonate buffer (50 mM; pH 9.5), and allowed to incubate at room temperature for 4 hours. Upon termination, 25 μL of a diethylenetriaminepentaacetic acid (DTPA) solution (0.25 M; pH 7.4) was added to scavenge the unbound ¹⁷⁷Lu. The labeled antibody was purified by centrifugal gel filtration chromatography. The purified labeled F(ab')2 which had been characterized by HPLC, SDS-PAGE analysis, and immunoreactivity assay, was used for biodistribution studies in Balb/C mice.

9D Preparation of ACL-2-Al-DOTA 177Lu F(ab')2 CC49

The labeled F(ab)2 CC49 was prepared and purified similarly as described in Example 9C, using the ACL-2-Al-DOTA ¹⁷⁷Lu complex from Example 9B. The labeled F(ab')2 was characterized and used for biodistribution studies in Balb/C mice.

9E Preparation of ACL-2-Ala-PA-DOTA 177Lu IgG CC49

The ¹⁷⁷Lu labeled IgG CC49 was prepared and purified in the same manner as described in Example 8C starting with the whole IgG CC49 as the antibody moiety, and used for in vitro cleavability evaluation.

9F - Preparation of ACL-2-Al-DOTA 177Lu IgG CC49

The ¹⁷⁷Lu labeled IgG CC49 was prepared and purified in the same manner as described in Example 9D starting with the whole IgG CC49 as the antibody moiety, and used for in vitro cleavability evaluation.

9G In Vitro Cleavability of ACL-2-Ala-PA-DOTA ¹⁷⁷Lu IgG CC49 and ACL-2-Al-DOTA ¹⁷⁷Lu IgG CC49

The cleavability of the acid cleavable linkers were evaluated at pH 4 and 6.0 in 0.2 M acetate buffer. Thus, the CC49 conjugates from Examples 8E and 8F were each incubated in the acetate buffer and analyzed at certain time intervals to determine the amount of $^{177}$Lu remained bound to the antibody. Results are given in Table

TABLE I

Cleavability of the Acid Cleavable Linkers When Conjugated to IgG CC49*

| Time | ACL-2-Ala-PA-DOTA | | ACL-2-Al-DOTA | |
|---|---|---|---|---|
| (Hour) | pH 6 | pH 4.0 | pH 6 | pH 4 |
| 0 | 98 | 98 | 99 | 99 |
| 14 | 92 | 57 | 96 | 77 |
| 20 | — | 47 | — | 71 |
| 37 | 86 | 40 | 95 | 63 |
| 66 | 82 | 30 | 82 | 51 |

*Determined as percent $^{177}$Lu Remaining Associatied with Antibody

EXAMPLE 10

Biodistribution Studies of PA-DOTA-$^{177}$Lu and $^{177}$Lu-ACL-2-Al-DOTA F(ab')$_2$ CC49

The conjugates utilizing ACL-2 were prepared as described in Example 8. The $^{177}$Lu-PA-DOTA F(ab')$_2$ CC49 was prepared as described in Example 8 with the substitution of the PA-DOTA for ACL-2-Ala-PA-DOTA.

In vivo localization of the 177Lu labeled conjugates was determined in Balb/c mice (purchased from Charles River Breeding Laboratories). Female Balb/c mice, approximately 13 weeks of age, were each injected via the tail vein with about 10 µCi $^{177}$Lu labeled conjugate in 50 µL of phosphate buffered saline (120 mM sodium chloride, 2.7 mM potassium chloride and 10 mM phosphate, pH 7.4). The mice were sacrificed at various time intervals. After exsanguination, the selected organs/tissues were excised, weighed and radioactivity measured in a gamma counter. The counts per minute (CPM) of $^{177}$Lu in each tissue was determined and expressed as CPM per gram of tissue per injected dose multiplies by 100 (percent injected dose/gram). Results for $^{177}$Lu-PA-DOTA CC49 F(ab')$_2$, $^{177}$Lu-ACL-2-PA-DOTA F(ab')$_2$ CC49 and $^{77}$Lu-ACL-2-Al-DOTA-F(ab')2 CC49, are given in Tables IIA IIB and IIC respectively.

TABLE IIA

Biodistribution of Lu-177-PA-DOTA-CC49-F(ab')2 in Balb/c Mice
Percent Injected Dose/Gram (n = 5)

| | 5 hours | | 24 Hours | | 46 Hours | | 120 Hours | |
|---|---|---|---|---|---|---|---|---|
| Tissue | Mean | Standard Deviation | Mean | Standard Deviation | Mean | Standard Deviation | Mean | Standard Deviation |
| Blood | 29.01 | 3.24 | 6.54 | 0.99 | 1.72 | 0.22 | 0.18 | 0.01 |
| Liver | 11.79 | 0.58 | 12.80 | 0.32 n = 4, a | 9.29 | 1.20 | 5.87 | 0.46 |
| Spleen | 9.34 | 0.27 n = 4 | 10.57 | 1.39 | 9.03 | 0.40 n = 4, a | 5.99 | 0.56 |
| Kidney | 46.46 | 4.74 | 99.67 | 9.51 | 76.42 | 9.44 | 35.00 | 3.05 |
| Femur | 2.79 | 0.21 | 3.41 | 0.48 | 2.65 | 0.42 | 2.00 | 0.22 |
| Whole Body Retention* | 91.00 | 5.11 | 82.78 | 1.49 | 58.02 | 3.39 | 25.30 | 1.39 |

*Whole Body retention is expressed as percent injected dose per organ

TABLE IIB

Biodistribution of Lu-177-ACL-2-Ala-PA-DOTA-CC49-F(ab')2 in Balb/c Mice
Percent Injected Dose/Gram (n = 5)

| | 5 hours | | 24 Hours | | 46 Hours | | 120 Hours | |
|---|---|---|---|---|---|---|---|---|
| Tissue | Mean | Standard Deviation | Mean | Standard Deviation | Mean | Standard Deviation | Mean | Standard Deviation |
| Blood | 19.70 | 0.95 | 5.81 | 0.95 | 1.85 | 0.50 | 0.15 | 0.02 |
| Liver | 8.38 | 0.62 | 8.99 | 1.26 | 7.79 | 1.34 | 5.86 | 0.68 |
| Spleen | 6.78 | 0.43 | 7.87 | 1.37 | 7.91 | 0.92 | 4.85 | 0.43 |
| Kidney | 38.57 | 0.83 | 78.75 | 11.39 | 65.24 | 6.98 | 35.26 | 4.13 |
| Femur | 1.76 | 0.14 n = 4, a | 2.52 | 0.63 | 2.32 | 0.53 | 1.50 | 0.21 |
| Whole Body Retention* | 76.98 | 2.46 | 60.78 | 3.98 | 48.66 | 2.62 | 25.32 | 1.18 |

*Whole body retention expressed as percent injected dose per organ.

TABLE IIC

| | Biodistribution of Lu-177-ACL-2-Al-DOTA-CC49-F(ab')2 in Balb/c Mice Percent Injected Dose/Gram (n = 5) | | | | | | | |
|---|---|---|---|---|---|---|---|---|
| | 5 hours | | 24 Hours | | 46 Hours | | 120 Hours | |
| Tissue | Mean | Standard Deviation | Mean | Standard Deviation | Mean | Standard Deviation | Mean | Standard Deviation |
| Blood | 27.10 | 2.58 | 7.32 | 1.11 | 2.38 | 0.31 | 0.23 | 0.03 |
| Liver | 11.45 | 1.03 | 13.25 | 2.06 | 9.99 | 0.77 | 5.99 | 0.49 |
| Spleen | 9.22 | 1.57 | 9.85 | 1.44 | 11.67 | 1.71 | 6.98 | 0.36 |
| Kidney | 46.06 | 4.50 | 90.51 | 11.64 | 85.46 | 6.64 | 44. | 2.09 |
| Femur | 2.78 | 0.43 | 3.05 | 0.31 | 2.64 | 0.14 n = 4 | 1.71 | 0.11 |
| Whole Body Retention* | 85.44 | 7.65 | 74.10 | 2.13 | 61.14 | 1.26 | 29.36 | 0.82 |

*Whole body retention is expressed as percent injected dose per organ.

The results indicate the following:

Blood

At the 5 hour time point the clearance of Lu-177 ACL-2-Ala PA-DOTA CC49 (F(ab')2 from the blood was significantly faster than the clearance of Lu-177 PA-DOTA CC49 F(ab')2. The clearance of ACL-2-Ala Pa-DOTA was also more rapid than Lu-177 ACL-2-AL DOTA CC49 F(ab')2 at 5 hours but this difference was not significant. At the other time points, the clearance of ACL-2-Ala PA-DOTA was somewhat faster than both PA-DOTA (except at 46 hours) and ACL-2-AL DOTA, but by five days the relative amount of radioactivity remaining in blood of mice treated with any of the three compounds was equivalent and negligible.

Liver, Spleen, Kidney, Femur, GI Tract, Carcass

Lower levels of lutetium were detected in the liver, spleen, kidney, femur, GI Tract and carcass of mice dosed with Lu-177 ACL-2-Ala PA-DOTA CC49 F(ab')2 in comparison to mice treated with either Lu-177 PA-DOTA CC49 F(ab')2 or Lu-177 ACL-2-AL DOTA CC49 F(ab')2. The kidney IDO values were subjected to analysis of variance testing. This comparison showed a significant decrease between the 24 hour and 46 hour kidney IDO values of ACL-2-Ala PA-DOTA when compared to either PA-DOTA or ACL-2-AL-DOTA. However, by 120 hours the amount of radioactivity remaining in the kidney tissues from animals dosed with ACL-2-Ala PA-DOTA and PA-DOTA were equivalent and both were significantly lower than kidney from ACL-2-AL DOTA treated mice.

Whole Body Retention

The whole body retention also reflected the very rapid clearance of ACL-2-Ala PA-DOTA. Clearance in the Lu-177 ACL-2-ALa PA-DOTA groups was significantly greater than PA-DOTA at the 5 hour, 24 hour, and 46 hour time points with the two compounds being equivalent at 5 days. Although Lu-177 ACL-2-Ala PA-DOTA CC49 F(ab')2 cleared more rapidly than Lu-177 ACL-2-AL DOTA CC49 F(ab')2 throughout the entire experiment, significant differences were seen only at the 24 hour, 46 hour, and 120 hour time points.

Overall, use of the acid cleavable linker, ACL-2-Ala-PA-DOTA appeared to increase the rate of clearance of lutetium labeled CC49 F(ab')2 in comparison to that of PA-DOTA, which is without the acid cleavable linker, and ACL-2-AL DOTA.

Other embodiments of the invention will be apparent to those skilled in the art from a consideration of the specification or practice of the invention disclosed herein. It is intended that the specification and examples be considered as exemplary only, with the true scope of and spirit of the invention being indicated by the following claims.

What is claimed is:

1. An heterobifunctional linker selected from the group of the following Formulae:

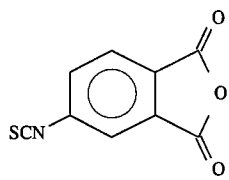

I

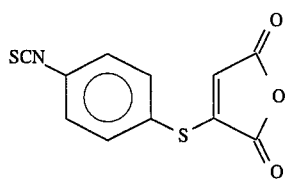

II and

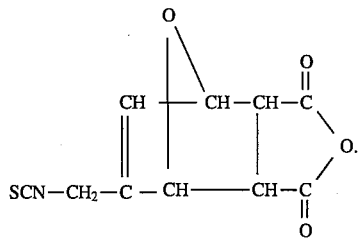

III

2. The linker of claim 1 wherein the linker is represented by Formula I as defined in claim 1.

3. The linker of claim 1 wherein the linker is represented by Formula II as defined in claim 1.

4. The linker of claim 1 wherein the linker is represented by Formula III as defined in claim 1.

* * * * *